(12) United States Patent
Matsubara

(10) Patent No.: US 9,808,604 B2
(45) Date of Patent: Nov. 7, 2017

(54) GUIDE WIRE

(71) Applicant: TERUMO KABUSHIKI KAISHA, Shibuya-ku, Tokyo (JP)

(72) Inventor: Yutaka Matsubara, Fujinomiya (JP)

(73) Assignee: Terumo Kabushiki Kaisha, Shibuya-ku, Tokyo (JP)

( * ) Notice: Subject to any disclaimer, the term of this patent is extended or adjusted under 35 U.S.C. 154(b) by 26 days.

(21) Appl. No.: 14/864,441

(22) Filed: Sep. 24, 2015

(65) Prior Publication Data

US 2016/0008586 A1  Jan. 14, 2016

Related U.S. Application Data

(63) Continuation of application No. PCT/JP2013/059833, filed on Apr. 1, 2013.

(51) Int. Cl.
*A61B 5/00* (2006.01)
*A61M 25/00* (2006.01)
*A61M 25/09* (2006.01)

(52) U.S. Cl.
CPC ..... *A61M 25/09* (2013.01); *A61M 2025/0915* (2013.01); *A61M 2025/09083* (2013.01); *A61M 2025/09091* (2013.01); *A61M 2025/09108* (2013.01); *A61M 2025/09175* (2013.01)

(58) Field of Classification Search
CPC ........ A61M 25/09; A61M 2025/09083; A61M 2025/0915; A61M 2025/09175
USPC ......................................................... 600/585
See application file for complete search history.

(56) References Cited

U.S. PATENT DOCUMENTS

| 5,042,475 A | 8/1991 | LaBombard | |
|---|---|---|---|
| 7,252,643 B2 * | 8/2007 | Fujimoto | A61M 25/09 600/585 |
| 7,789,839 B2 * | 9/2010 | Lupton | A61M 25/09 600/585 |

(Continued)

FOREIGN PATENT DOCUMENTS

| JP | 7-500022 A | 1/1995 |
|---|---|---|
| JP | 2007-501648 A | 2/2007 |

(Continued)

OTHER PUBLICATIONS

Japanese Official Action "Notice of Reasons for Rejection" dated Apr. 12, 2016 by the Japanese Patent Office in the counterpart Japanese Application No. 2015-509630 with complete English translation (6 pages).

(Continued)

*Primary Examiner* — Devin Henson
(74) *Attorney, Agent, or Firm* — Buchanan, Ingersoll & Rooney PC

(57) ABSTRACT

A guide wire includes a wire main body that has a plate-like portion in a distal end portion of the wire main body and a reinforcement portion that is provided on at least one surface of the plate-like portion and reinforces the plate-like portion. The reinforcement portion is made up of two wire rods, and both end portions of the reinforcement portion are fixed to the plate-like portion. The plate-like portion is formed in a ribbon shape, and the reinforcement portions are diagonally provided on the same plane of the plate-like portion, and intersect each other. The guide wire has a coil that covers the plate-like portion and the reinforcement portion.

10 Claims, 3 Drawing Sheets

(56) References Cited

U.S. PATENT DOCUMENTS

2006/0264784 A1 11/2006 Lupton
2007/0032744 A1* 2/2007 Lupton ................ A61M 25/09
600/585

FOREIGN PATENT DOCUMENTS

| JP | 2012-005722 A | 1/2012 |
| WO | 93/00124 A1 | 1/1993 |
| WO | 2005/014095 A1 | 2/2005 |

OTHER PUBLICATIONS

International Search Report (PCT/ISA/210) dated Jun. 11, 2013, by the Japanese Patent Office as the International Searching Authority for International Application No. PCT/JP2013/059833.

* cited by examiner

GUIDE WIRE

CROSS-REFERENCE TO RELATED APPLICATION

This application is a continuation of International Application No. PCT/JP2013/059833 filed on Apr. 1, 2013, the entire content of which is incorporated herein by reference.

TECHNICAL FIELD

The present invention relates to a guide wire.

BACKGROUND DISCUSSION

A guide wire is used to introduce and guide a catheter, for example, which is used in the treatment of a portion of the body on which it is difficult to perform surgery, in minimal invasive treatment for a human body, or in angiographic examination and treatment for heart disease, to a target portion.

When percutaneous coronary intervention (PCI) or the like is performed, a guide wire along with a balloon catheter is inserted into the front of a stenotic portion of a coronary artery, that is, a target portion, while a distal end of the guide wire protrudes further than a distal end of the balloon catheter, the distal end of the guide wire passes through the stenotic portion, a balloon of the balloon catheter is guided to the stenotic portion along the guide wire, and the balloon is inflated to open the stenotic portion, thereby allowing blood to flow.

In order for the guide wire to be able to be inserted from a femoral artery and move forward to the coronary artery via an aorta, an aortic arch, a coronary ostium or the like using a Seldinger technique, the guide wire is preferably good in flexibility (followability) required to track a blood vessel, pushing performance (pushability) by which a pushing force applied on a proximal portion is effectively transmitted to a distal end portion, and torque transmission performance by which a rotating force applied on a proximal end side of the guide wire is reliably transmitted to a distal end side of the guide wire.

In order to select an appropriate branch of a junction of the coronary artery or the like using the guide wire, and to move the guide wire forward, a distal end portion of the guide wire may be deformed to the shape of the junction. Typically, the deformation is performed by the fingers of a doctor or other personnel during an operation, and is referred to as reshaping.

In particular, when the distal end of the guide wire is inserted into a distal coronary artery, it is not possible to select a desired branch using a guide wire with a pre-formed angled or a J-shaped distal end as known in the art, and in many cases, the distal end of the guide wire is changed to the desired shape, and the guide wire is re-inserted. When the distal end of the guide wire is still not fitted to the desired shape, the guide wire has to be removed from the catheter, be re-shaped, and then be inserted. Accordingly, the distal end portion of the guide wire is required to have flexibility along with reshaping performance.

There is known in the art to have a flat portion of the distal end portion being formed in a plate shape so as to obtain flexibility of the distal end portion of the guide wire (for example, as shown in JP-A-2012-5722).

Since the flat portion of the guide wire disclosed in JP-A-2012-5722 is formed in a plate shape, it is possible to bend the flat portion in a thickness direction. That is, the flat portion has good flexibility. The flat portion has sufficient flexibility, however, in contrast, the plate-like flat portion has relatively low torsional rigidity. Accordingly, there is a problem in that torque transmission performance is not sufficient. Since the flat portion has sufficient flexibility but low torsional rigidity, when the guide wire is pushed toward the distal end side, the flat portion may buckle, which is a problem. In the guide wire in the related art, flexibility, torque transmission performance, and pushing performance have not been compatible with each other.

SUMMARY

The disclosure herein provides a guide wire in which it is possible to obtain good torque transmission performance and pushing performance while sufficiently ensuring flexibility of a distal end portion of the guide wire.

According to an exemplary embodiment of the disclosure, a guide wire includes: a wire main body that has a plate-like portion in a distal end portion of the wire main body; and a reinforcement portion that is provided on at least one surface of the plate-like portion, and reinforces the plate-like portion.

In the guide wire according to another aspect of the disclosure, the reinforcement portion is made up of at least one wire rod.

Still further, in another aspect of the disclosure, both end portions of the reinforcement portion are fixed to the plate-like portion of the guide wire.

Another aspect of the disclosure is directed to the plate-like portion of the guide wire being formed in a ribbon shape, and the reinforcement portion being provided on a diagonal line of the plate-like portion.

In a further aspect of the disclosure, the reinforcement portions are provided on both surfaces of the plate-like portion.

Still further, in the guide wire according to another aspect of the disclosure, the reinforcement portion is made up of two wire rods, and the two wire rods are provided on the same plane of the plate-like portion, and intersect each other.

In another aspect of the disclosure, the reinforcement portion is made up of two wire rods, and the two wire rods are provided on both surfaces of the plate-like portion, and intersect each other in a plan view.

In another aspect of the disclosure of the guide wire, the plate-like portion is formed in a ribbon shape, and the reinforcement portion is made up of at least one wire rod that extends in a longitudinal direction, and at least one wire rod that extends in a lateral direction.

Still further, according to another aspect of the disclosure, the rigidity of the reinforcement portion in the guide wire is the same as that of the plate-like portion.

In another aspect of the disclosure, the rigidity of the reinforcement portion is different from that of the plate-like portion.

Another aspect of the disclosure is directed to the reinforcement portion being configured as a member that is separate from the plate-like portion.

In another aspect of the disclosure, the reinforcement portion is formed integrally with the plate-like portion.

According to a further aspect of the disclosure, the guide further includes: a coil that covers the plate-like portion and the reinforcement portion.

According to an exemplary embodiment of the disclosure, it is possible to easily and reliably deform the distal end portion of the guide wire in a desired shape while sufficiently ensuring the flexibility of the distal end portion of the guide wire, and to provide the guide wire with good torque transmission performance and pushing performance.

In particular, it is possible to ensure the flexibility, the torque transmission performance, and the pushing performance of the distal end portion of the guide wire by providing at least one wire rod on at least one surface of the plate-like portion.

DETAILED DESCRIPTION

Hereinafter, preferred exemplary embodiments of a guide wire of the disclosure will be described in detail with reference to the accompanying drawings.

Figure 1:
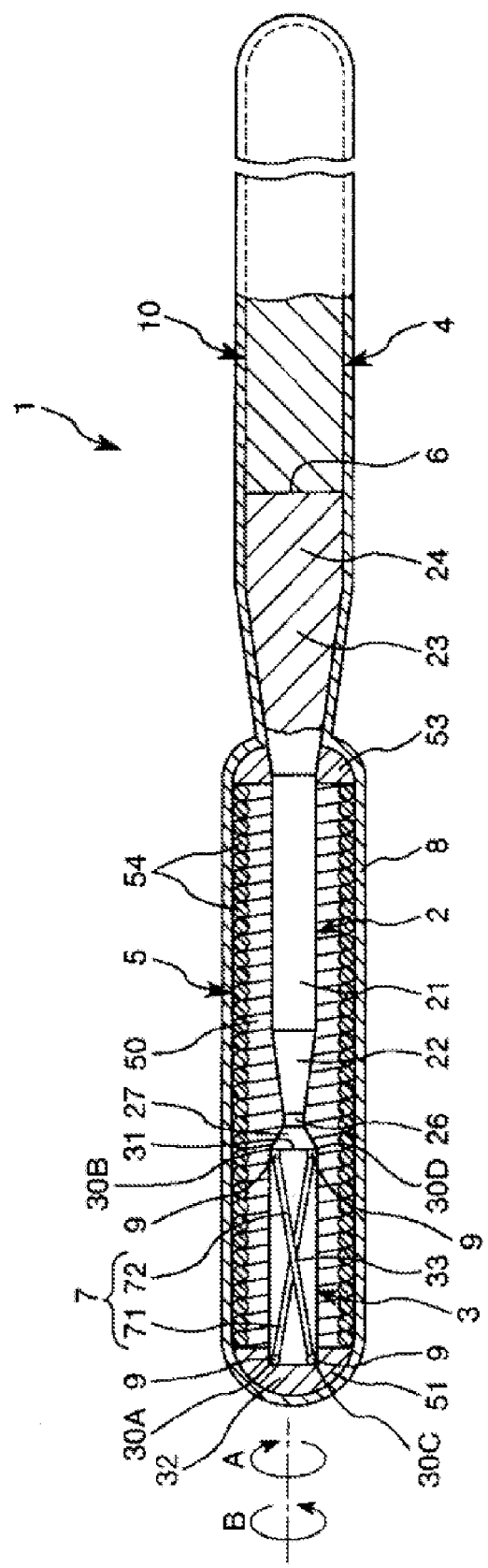
FIG. 1 is a partial longitudinal sectional view (schematic side view) of a guide wire according to a first exemplary embodiment of the disclosure.

FIG. 1 is a partial longitudinal sectional view (schematic side view) of a guide wire in a first exemplary embodiment of the disclosure herein. Hereinafter, for illustrative purposes, in FIG. 1, the right side and the left side in a longitudinal direction of the guide wire are respectively referred to as a "proximal end" and a "distal end", and an upper side and a lower side are respectively referred to as the "top" and the "bottom". In FIG. 1, for ease of understanding, the guide wire is schematically illustrated in a state where the longitudinal length of the guide wire is reduced, and the radial length (thickness) of the guide wire is increased, and the ratio of the longitudinal length to the radial length is different from an actual ratio (the same also applies to FIGS. 2 and 3).

A description of the exemplary embodiments will be given below based on the understanding that a thickness direction of a plate-like portion is a direction in which the guide wire is bent when re-shaped.

A guide wire 1 illustrated in FIG. 1 is a guide wire for a catheter (or an endoscope) which is used while being inserted into the bore of a catheter, and has a wire main body 10 in which a second wire 4, disposed on a proximal end side of a first wire 2, is joined to the first wire 2 that is disposed on a distal end side and which has a plate-like portion 3; a helical coil 5 that is disposed on a distal end portion (portion on a distal end side) of the wire main body 10; and a reinforcement portion 7 that reinforces the plate-like portion 3. Although the entire length of the guide wire 1 is not limited to a specific dimension, the guide wire 1 preferably has a total length of approximately 200 mm to 5000 mm.

The first wire 2 is made of a wire rod with flexibility or elasticity. In the first exemplary embodiment, the first wire 2 has a constant outer-diameter portion 21 that has a substantially constant outer diameter; a first tapered portion 22 which is positioned closer to the distal end side than the constant outer-diameter portion 21, and the outer diameter of which gradually decreases toward a distal end; a distal-end constant outer-diameter portion 26 that is positioned closer to the distal end side than the first tapered portion 22; a plate-like transition portion 27 which is positioned on a distal end side of the distal-end constant outer-diameter portion 26, the thickness of which decreases toward the distal end, and the width of which increases toward the distal end; a plate-like portion 3 that is positioned on a distal end side of the plate-like transition portion 27; a large-diameter portion 24 that is positioned closer to the proximal end side than the constant outer-diameter portion 21, and has an outer diameter which is larger than that of the constant outer-diameter portion 21; and a second tapered portion 23 which is positioned between the constant outer-diameter portion 21 and the large-diameter portion 24, and the outer diameter of which gradually decreases toward the distal end. The following portions are sequentially disposed from the distal end side to the proximal end side of the first wire 2: the plate-like portion 3; the transition portion 27; the distal-end constant outer-diameter portion 26; the first tapered portion 22; the constant outer-diameter portion 21; the second tapered portion 23; and the large-diameter portion 24.

Since the first tapered portion 22 is formed between the plate-like portion 3 and the constant outer-diameter portion 21, and more particularly, since the plate-like portion 3 is formed in the vicinity of the distal end side of the first tapered portion 22, it is possible to gradually decrease the rigidity (flexural rigidity, torsional rigidity) of the first wire 2 toward the proximal end, and thus, a distal end portion of the guide wire 1 can have good properties of being able to be passed through a stenotic portion, and flexibility. Therefore, the guide wire 1 can have an improved ability of being able to follow a blood vessel or the like, can improve safety, and can be prevented from being kinked, for example.

Similar to the first tapered portion 22, since the second tapered portion 23 is interposed between the constant outer-diameter portion 21 and the large-diameter portion 24, it is possible to gradually decrease the rigidity (flexural rigidity, torsional rigidity) of the first wire 2 toward the distal end.

The taper angle (reduction rate in the outer diameter) of the first tapered portion 22 (and the second tapered portion 23) may be constant or be changed along a longitudinal direction of the wire main body 10. For example, regions formed with a relatively large taper angle (reduction rate in the outer diameter) and regions formed with a relatively small taper angle may be alternately repeated multiple times.

The first tapered portion 22 and the second tapered portion 23 may have different tapered shapes and taper angles.

Preferably, the plate-like portion 3 with the following configuration is integrally formed on a distal end side of the first tapered portion 22 while the distal-end constant outer-diameter portion 26 and the transition portion 27 are interposed between the plate-like portion 3 and the first tapered portion 22. According to the first exemplary embodiment, the entirety of the first wire 2 including the plate-like portion 3 is integrally made of the same material, and the first wire 2 is preferably made of a superelastic alloy (alloy with pseudoelasticity) that is represented by a Ni—Ti alloy, which will be described later. For this reason, the plate-like portion 3 is preferably made of a superelastic alloy, and hereinafter, this case will be described.

As illustrated in FIG. 1, the plate-like portion 3 is formed in a plate shape (ribbon or planar shape), and it is possible to use the plate-like portion 3 in a state where the shape of the plate-like portion 3 is changed (referred to as "re-shaped or shaped") to a desired shape. Typically, a doctor or other personnel uses the guide wire in a state where the shape of the distal end portion of the guide wire is changed to a predetermined desired shape so that a distal end portion of a guiding catheter or the like can be adapted to the shape of a blood vessel, or a blood vessel branch can be selected and guided appropriately and smoothly. As such, the bending of the distal end portion of the guide wire in a desired shape is referred to as the term "reshaping". Since the plate-like portion 3 is provided, it is possible to easily and reliably re-shape the guide wire 1, and to considerably improve operability when the guide wire 1 is inserted into a living body.

In the exemplary embodiment, the width of the plate-like portion 3 is substantially constant along a longitudinal direction of the plate-like portion 3. The width of the plate-like portion 3 is not limited to a specific value insofar as the width is set such that the plate-like portion 3 is accommodated in the internal space (a gap 50) of the coil 5. In order to ensure sufficient flexibility and appropriate strength, the plate-like portion 3 preferably has a width of approximately 0.05 mm to approximately 0.3 mm, and more preferably has a width of approximately 0.15 mm to approximately 0.25 mm.

In the exemplary embodiment, the thickness of the plate-like portion 3 is substantially constant along the longitudinal thereof. The thickness of the plate-like portion 3 is not limited to a specific value, and in order to ensure sufficient flexibility and appropriate strength, the plate-like portion 3 preferably has a thickness of approximately 0.01 mm to approximately 0.06 mm, and more preferably has a thickness of approximately 0.02 mm to approximately 0.04 mm.

In the first wire 2, the outer diameter of each of the distal-end constant outer-diameter portion 26, the constant outer-diameter portion 21, and the large-diameter portion 24 is constant along a longitudinal direction of the wire. The outer diameter of the distal-end constant outer-diameter portion 26 is substantially the same as the minimum outer diameter of the first tapered portion 22, and the outer diameter of the constant outer-diameter portion 21 is substantially the same as the maximum outer diameter of the first tapered portion 22, and is substantially the same as the minimum outer diameter of the second tapered portion 23. The outer diameter of the large-diameter portion 24 is substantially the same as the maximum outer diameter of the second tapered portion 23.

A proximal end of the first wire 2 (a proximal end of the large-diameter portion 24) is joined to a distal end of the second wire 4. The second wire 4 is made of a wire rod with flexibility or elasticity.

A method of joining the first wire 2 to the second wire 4 is not limited to a specific method, and the first wire 2 may be joined to the second wire 4 using, for example, welding such as friction pressure welding, spot welding using a laser beam, butt resistance welding such as upset welding, or the like, or a tubular joining member. In particular, the butt resistance welding is preferably used because it is possible to relatively simply obtain high joining strength.

In the exemplary embodiment, the outer diameter of the second wire 4 is substantially constant. The outer diameter of the second wire 4 is substantially the same as that of the large-diameter portion 24 of the first wire 2. Accordingly, when the proximal end of the large-diameter portion 24 of the first wire 2 is joined to the distal end of the second wire 4, it is possible to form a continuous surface on the outer circumference of a joined portion (welded portion) 6 without the formation of a step that is induced by the difference in the outer diameter between both wires 2 and 4. The present invention is not limited to the aforementioned configuration, and the first wire 2 and the second wire 4 may have different outer diameters before and after the joined portion 6.

The mean outer diameter of the first wire 2 is smaller than that of the second wire 4. Accordingly, since the guide wire 1 is configured such that the first wire 2 on the distal end side of the guide wire 1 has good flexibility, and the second wire 4 on the proximal end side thereof has relatively high rigidity, the flexibility of the distal end portion can be compatible with good operability (pushing performance, torque transmission performance, and the like).

The material of the first wire 2 and the second wire 4 is not limited to a specific material, and it is possible to use, for example, various metal materials such as stainless steel (for example, all types of SUS such as SUS304, SUS303, SUS316, SUS316L, SUS316J1, SUS316J1L, SUS405, SUS430, SUS434, SUS444, SUS429, SUS430F, SUS302, or the like), piano wire, cobalt alloys, alloys with pseudoelasticity (including a superelastic alloy), and the like.

A pseudoelastic alloy (including a superelastic alloy) is preferably used as the material of the first wire 2, and a superelastic alloy is more preferably used.

Since the first wire 2 is made of the superelastic alloy which has good flexibility and resilience, and is unlikely to have a tendency to bend, the distal end portion of the guide wire 1 can have sufficient flexibility, and resilience against bending. Therefore, it is possible to obtain an improved ability of being able to follow complex curved and bent blood vessels or the like, and to obtain better operability. Since the first wire 2 is unlikely to have a bend tendency due to the resilience of the first wire 2, even if the first wire 2 repeatedly undergoes curving and bending deformation, the bend tendency of the first wire 2 of the guide wire 1 in use can be prevented from causing deterioration in the operability.

The pseudoelastic alloys includes pseudoelastic alloys with any tensile stress-strain curves, pseudoelastic alloys in which the transformation point of As, Af, Ms, Mf, or the like can be or cannot be measured in a distinguishing manner, and pseudoelastic alloys which are considerably deformed (distorted) due to stress, and substantially return to their original shape when the stress is removed.

With regard to the compositions of the superelastic alloys exemplified herein, preferably, a Ni—Ti alloy such as a Ni—Ti alloy containing 49% to 52% of Ni atoms, or the like, a Cu—Zn alloy containing 38.5% to 41.5% by weight of Zn, a Cu—Zn—X alloy containing 1% to 10% by weight of X (X is at least one type of Be, Si, Sn, Al, and Ga), a Ni—Al alloy containing 36% to 38% of Al atoms, and the like can be used. In particular, the Ni—Ti alloy among these alloys is preferably used. The superelastic Ni—Ti alloy has good adhesion to a resin coating layer 8 (to be described later).

A wire made of a cobalt alloy has a high elastic modulus, and an appropriate elastic limit. For this reason, the wire made of the cobalt alloy has good torque transmission performance, and is very unlikely to experience buckling or the like. Any cobalt alloy may be used insofar as the cobalt alloy contains Co as a configurational element, the cobalt alloy preferably contains Co as a main component (Co-based alloy: alloy which has the highest content of Co by weight ratio among the elements of the alloy), and a Co—Ni—Cr alloy is more preferably used. The aforementioned effects become more distinguished when the alloys with these compositions are used. The alloys with these compositions can be cold-formed even if these alloys have a high coefficient of elasticity, and a high elastic limit. Since these alloys have a high elastic limit, it is possible to satisfactorily prevent the occurrence of buckling, to reduce the diameter of the wire, and to have flexibility and rigidity required to insert the wire into a predetermined portion.

Stainless steel is preferably used as the material of the second wire 4. The stainless steel has strength and rigidity that is higher than those of the superelastic alloy, and for this reason, good pushing performance and good torque transmission performance can be provided to the guide wire 1.

The first wire 2 and the second wire 4 may be made of different materials, or may be made of the same or the same type of metal material (the main metal materials of alloys are the same). In the latter case, joining strength of the joined portion (welded portion) 6 further increases, and even if the outer diameter of the joined portion 6 is decreased, it is possible to exhibit good torque transmission performance or the like without causing separation or the like.

When the first wire 2 and the second wire 4 are made of different materials, preferably, the first wire 2 is made of the superelastic alloy, and in particular, is made of the Ni—Ti alloy, and the second wire 4 is preferably made of stainless steel.

In the aforementioned case, the first wire 2 is joined to the second wire 4; however, the first wire 2 and the second wire 4 may be integrally formed as a single wire main body that is continuously formed without a joined portion. In this case, the aforementioned same materials are used as the material of the wire main body, and in particular, stainless steel, a cobalt alloy, or a pseudoelastic alloy is preferably used.

The coil 5 is disposed on an outer circumference of the distal end portion of the wire main body 10 in such a way as to cover the distal end portion and the plate-like portion 3. A contact area between the surface of the wire main body 10 and an inner wall of the catheter or between the surface of the wire main body 10 and the surface of a living body decreases due to the installation of the coil 5, and thus, it is possible to reduce slide resistance. As a result, the operability of the guide wire 1 is improved.

As illustrated in FIG. 1, the wire main body 10 is inserted into an inner center portion of the coil 5. In the exemplary embodiment, the coil 5 covers the plate-like portion 3, the transition portion 27, the distal-end constant outer-diameter portion 26, the first tapered portion 22, and all or portions of the constant outer-diameter portion 21.

The distal end portion (particularly, a region from the plate-like portion 3 to the first tapered portion 22) of the wire main body 10 is inserted into the coil 5 while not being in contact with the inner surface of the coil 5. Accordingly, the gap 50 is formed between the coil 5 and the distal end portion of the wire main body 10.

The coil 5 is made by helically forming a wire 54 with a circular cross section. In this case, a single wire 54 may be helically wound, or a plurality of wires 54 may be helically wound.

The material of the wire 54 is not limited to a specific material, and the wire 54 may be made of either one of a metal material and a resin material. The following materials are preferably used as the metal material: stainless steel, or radiopaque materials such as noble metals (for example, Au and Pt) and alloys (for example, Pt—Ni alloy) containing these noble metals. In the latter case, the distal end portion of the guide wire 1 can be X-ray imaged, and it is possible to insert the guide wire 1 into the living body while confirming the position of the distal end portion under X-ray fluoroscopy, which is preferable.

The coil 5 may be made of a combination of two or more materials. For example, a portion of the wire 54 on a distal end side of the coil 5 can be made of a radiopaque material such as the Pt—Ni alloy, and a portion of the wire 54 on a proximal end side of the coil 5 can be made of stainless steel. In this case, a portion (a portion that particularly includes the plate-like portion 3) on the distal end side of the coil 5 under X-ray fluoroscopy can be emphasized (more easily visualized) than a portion that is positioned closer to the proximal end side than the portion on the distal end side, and thus it is possible to more clearly visualize a foremost end portion (a portion in which the plate-like portion 3 is present) of the guide wire 1.

The disclosure here is not limited to a case in which the coil 5 covers a region from the plate-like portion 3 to the constant outer-diameter portion 21 as illustrated, and the coil 5 may cover portions of one or more of the plate-like portion 3, the transition portion 27, the distal-end constant outer-diameter portion 26, the first tapered port 22, and the constant outer-diameter portion 21. In this case, the coil 5 preferably covers at least an outer circumference of the plate-like portion 3.

When the coil 5 is disposed on the outer circumference of the plate-like portion 3, the coil 5 may be in contact or close contact with the plate-like portion 3, and the coil 5 may be disposed so that a portion of the guide wire 1, in which the plate-like portion 3 is present, can be X-ray imaged.

The wire diameter of the wire 54 of the coil 5 may be constant over the entire length of the coil 5, or the wire diameters of the wire(s) 54 on the distal end side and the proximal end side of the coil 5 may be different. For example, the wire diameter of the wire 54 on the distal end side of the coil 5 may be smaller (greater) than that of the wire 54 on the proximal end side. Accordingly, it is possible to further improve the flexibility of the guide wire 1 in a distal end portion of the coil 5.

The outer diameter of the coil 5 may be the same over the entire length of the coil 5, or the outer diameters of the coil 5 on the distal end side and the proximal end side of the coil 5 may be different. For example, the outer diameter of the coil 5 on the distal end side of the coil 5 may be smaller than that of the coil 5 on the proximal end side. Accordingly, it is possible to further improve the flexibility of the guide wire 1 in the distal end portion of the coil 5.

In the exemplary embodiment, the adjacent wires 54 of the coil 5 are in contact with each other, that is, the wires 54 are densely wound. In a no-load state, a force (compression force) pushing the wires 54 against each other in an axial direction of the wire main body 10 is generated. Here, the term "no-load state" refers to a state in which an external force is not applied. The disclosure is not limited to a case in which the wires 54 are densely wound, and there may be gaps present between the adjacent wires 54 of the coil 5.

As illustrated in FIG. 1, the coil 5 is fixed to the wire main body 10 at two locations (multiple locations). That is, the distal end portion of the coil 5 is fixed to the distal end of the first wire 2 (the distal end of the plate-like portion 3) using a fixing material 51, and a proximal end portion of the coil 5 is fixed to the middle (the vicinity of the boundary between the constant outer-diameter portion 21 and the second tapered portion 23) of the first wire 2 using a fixing material 53. Due to the coil 5 being fixed at these locations, it is possible to reliably fix the portions of the coil 5 to the wire main body 10 without decreasing the flexibility of the distal end portion (a portion in which the coil 5 is present) of the guide wire 1. In addition, it is possible to reliably fix the plate-like portion 3 to the coil 5, and to appropriately maintain the shape of the plate-like portion 3 which has been shaped.

Solder (brazing material) is preferably used as each of the fixing materials 51 and 53. Each of the fixing materials 51 and 53 are not limited to solder, and may be an adhesive. A method of fixing the coil 5 to the wire main body 10 is not limited to the use of the aforementioned fixing materials, and may be welding. A distal end surface of the fixing material 51 is preferably rounded so as to prevent an inner wall of a body cavity such as a blood vessel or the like from being damaged (refer to FIG. 1).

As illustrated in FIG. 1, the resin coating layer 8 is provided on the outer surface of the guide wire 1 in such a way as to cover the entirety (or a portion) of the guide wire 1. The resin coating layer 8 can be formed for various purposes, and for example, the friction (slide resistance) of the guide wire 1 is reduced, and sliding performance is improved, and thus the operability of the guide wire 1 is improved.

In order to reduce the friction (slide resistance) of the guide wire 1, the resin coating layer 8 is preferably made of friction reduction materials which will be described hereinbelow. Accordingly, friction resistance (slide resistance) between the guide wire 1 and the inner wall of the catheter in use therewith is reduced, and thus the sliding performance of the guide wire 1 is improved, and the operability of the guide wire 1 in the catheter is further improved. Since the slide resistance of the guide wire 1 is reduced, it is possible to more reliably prevent the occurrence of a kink (bending) or twist of the guide wire 1, and particularly, the occurrence of a kink or twist in the vicinity of the joined portion 6 when the guide wire 1 moves or rotates in the catheter.

The following materials are exemplified as the friction reduction materials: polyolefin such as polyethylene, polypropylene, or the like; polyvinyl chloride; polyester (PET, PBT, or the like); polyamide; polyimide; polyurethane; polystyrene; polycarbonate; silicone resin; fluorine-based resin (PTFE, ETFE, or the like); and a composite material which is a combination of these materials.

The resin coating layer 8 can be provided so as to improve safety when the guide wire 1 is inserted into a blood vessel or the like. For this reason, the resin coating layer 8 is preferably made of a material (soft material or elastic material) with good flexibility.

The following materials are exemplified as the materials with good flexibility: polyolefin such as polyethylene, polypropylene, or the like; polyvinyl chloride; polyester (PET, PBT, or the like); polyamide; polyimide; polyurethane; polystyrene; silicone resin; thermoplastic elastomers such as polyurethane elastomer, polyester elastomer, polyamide elastomer or the like; various rubber materials such as latex rubber, silicone rubber, or the like; a composite materials which is a combination of two or more of these materials; and the like.

The present invention is not limited to a case in which the entire resin coating layer 8 is made of the same material, and the material of the resin coating layer 8 may be changed in the middle of the resin coating layer 8 in a longitudinal direction of the guide wire 1. For example, a portion of the resin coating layer 8, with which the first wire 2 and the coil 5 are covered, can be made of an aforementioned material with good flexibility, and a portion of the resin coating layer 8, with which the second wire 4 is covered, can be made of an aforementioned friction reduction material.

The resin coating layer 8 may be configured as a single layer, or may be configured as a laminated body (for example, in which an inner layer is made of a material that is more flexible than the material of an outer layer) with two or more layers. For example, the portion of the resin coating layer 8, with which the first wire 2 and the coil 5 are covered, can be configured as a single layer, and the portion of the resin coating layer 8, with which the second wire 4 is covered, can be configured as a laminated body with two or more layers. This configuration may be reversed.

A groove (not illustrated) may be formed on the outer circumferential surface of the resin coating layer 8. In particular, the resin coating layer 8 is preferably provided with a groove with a straight pattern, a curved pattern, a ring-shaped pattern, a helical pattern, a net-shaped pattern, or the like which is disposed to correspond to at least the plate-like portion 3 (in an outer circumferential portion of the plate-like portion 3). Due to the formation of the groove, it is possible to increase the flexibility of the distal end portion of the guide wire 1 and to reduce the friction (slide resistance) of the guide wire 1, and thus it is possible to further improve the sliding performance of the guide wire 1.

The outer surface of at least the distal end portion of the guide wire 1 is preferably coated with a hydrophilic material. Accordingly, lubricating performance is obtained due to wetness of the hydrophilic material, the friction (slide resistance) of the guide wire 1 is reduced, and the sliding performance is improved. As a result, the operability of the guide wire 1 is improved.

The following materials are exemplified as the hydrophilic materials: a cellulosic polymer, a polyethylene oxide polymer; a maleic anhydride polymer (for example, maleic anhydride copolymer such as methyl vinyl ether-maleic anhydride copolymer); an acrylamide polymer (for example, polyacrylamide, and polyglycidyl methacrylate-dimethyl acrylamide (PGMA-DMAA) block copolymer); water-soluble nylon; polyvinyl alcohol; polyvinylpyrrolidone; and the like.

In many cases, these hydrophilic materials show lubricating performance due to wetness (water absorption), and reduce friction resistance (slide resistance) between the guide wire 1 and the inner wall of the catheter in use therewith. Accordingly, the sliding performance of the guide wire 1 is improved, and the operability of the guide wire 1 in the catheter is further improved.

According to an exemplary embodiment of the disclosure, the reinforcement portion 7 is provided on one surface of the plate-like portion 3 of the guide wire 1 such that the plate-like portion 3 is reinforced. The reinforcement portion 7 works as a rigidity providing portion that provides rigidity to the plate-like portion 3 with good flexibility.

As illustrated in FIG. 1, the reinforcement portion 7 is linearly formed, and has a first wire rod 71 and a second wire rod 72 which are formed separately from the plate-like portion 3. The first wire rod 71 and the second wire rod 72 preferably have a circular cross section, and are provided on the same plane. In the disclosure here, the cross section of each of the first wire rod 71 and the second wire rod 72 is not limited to a specific shape, and may have any one of an elliptical shape, a rectangular shape, a semicircular shape, and the like. The wire diameter (thickness) of each of the first wire rod 71 and the second wire rod 72 is constant along a longitudinal direction thereof.

The first wire rod 71 is positioned on a diagonal line that connects a left upper corner 30A and a right lower corner 30D of the plate-like portion 3 as illustrated in FIG. 1. In contrast, the second wire rod 72 is positioned on a diagonal line that connects a left lower corner 30C and a right upper corner 30B of the plate-like portion 3 as illustrated in FIG. 1.

A distal end portion of the first wire rod 71 is fixed to the corner 30A, and a proximal end portion of the first wire rod 71 is fixed to the corner 30D. In contrast, a distal end portion of the second wire rod 72 is fixed to the corner 30C, and a proximal end portion of the first wire rod 71 is fixed to the corner 30B. The first wire rod 71 and the second wire rod 72 intersect each other in a center portion of the plate-like portion 3.

When a rotating force is applied to a proximal end portion of the guide wire 1, the rotating force is transmitted from the proximal end side, to the second wire 4, to the first wire 2, and then to the distal end side of the guide wire 1. When the rotating force is transmitted to a proximal end 31 of the plate-like portion 3, the rotating force is transmitted from the proximal end 31 of the plate-like portion 3 to a distal end 32. Since the plate-like portion 3 with good flexibility is likely to be elastically deformed (is likely to be twisted) in this process, the transmission of the rotating force is insufficient, which is a problem. However, in the disclosure herein, the rotating force transmitted to the proximal end 31 of the plate-like portion 3 is sufficiently transmitted to the distal end of the plate-like portion 3 via the first wire rod 71 and the second wire rod 72. Specifically, when the guide wire 1 is rotated in a direction of arrow A in FIG. 1, the second wire rod 72 is mainly responsible for the transmission of the rotating force, and the rotating force is sufficiently transmitted to the distal end 32 of the plate-like portion 3 via the second wire rod 72. In contrast, when the guide wire 1 is rotated in a direction of arrow B in FIG. 1, the first wire rod 71 is mainly responsible for the transmission of the rotating force, and the rotating force is sufficiently transmitted to the distal end 32 of the plate-like portion 3 via the first wire rod 71. Accordingly, it is possible to sufficiently and reliably transmit torque to the distal end of the guide wire 1.

When a pushing force is applied from the proximal end portion of the guide wire 1 to the distal end portion of the guide wire 1, the pushing force is transmitted from the proximal end side, to the second wire 4, to the first wire 2, and then to the distal end side of the guide wire 1. When the pushing force is transmitted to the proximal end 31 of the plate-like portion 3, the pushing force is transmitted from the proximal end 31 of the plate-like portion 3 to the distal end 32. The plate-like portion 3 with good flexibility may buckle in this process, which is a problem. However, in the disclosure herein, the first wire rod 71 and the second wire rod 72 are responsible for the transmission of the pushing force. The pushing force transmitted to the proximal end 31 of the plate-like portion 3 is sufficiently transmitted to the distal end of the plate-like portion 3 via the first wire rod 71 and the second wire rod 72. Accordingly, the plate-like portion 3 has good pushing performance (pushability).

Both end portions of each of the first wire rod 71 and the second wire rod 72 are fixed to the plate-like portion 3 using fixing portions 9. In other words, portions of the first wire rod 71 and the second wire rod 72 other than the both end portions can approach and move away from the surface of the plate-like portion 3. The first wire rod 71 and the second wire rod 72 are not fixed at an intersection portion 33 in which the first wire rod 71 and the second wire rod 72 intersect each other. Accordingly, the first wire rod 71 and the second wire rod 72 can be independently deformed. As a result, the first wire rod 71 and the second wire rod 72 can be easily deformed to follow deformation of the plate-like portion 3. It is possible to prevent deterioration in the reshaping properties of the plate-like portion 3.

Each of the first wire rod 71 and the second wire rod 72 preferably has a length of 3 mm to 30 mm, and more preferably has a length of 5 mm to 20 mm. In the exemplary embodiment, the length of the first wire rod 71 is the same as that of the second wire rod 72; however, the first wire rod 71 and the second wire rod 72 may have different lengths.

Each of the first wire rod 71 and the second wire rod 72 preferably has a wire diameter of 0.03 mm to 0.15 mm, and more preferably has a wire diameter of 0.05 mm to 0.1 mm.

In the disclosure here, the wire diameter of each of the first wire rod 71 and the second wire rod 72 is constant along the longitudinal direction thereof; however, the wire diameter may be changed in the middle of each of the first wire rod 71 and the second wire rod 72 along the longitudinal direction. For example, when each of the first wire rod 71 and the second wire rod 72 is configured such that the wire diameter gradually decreases toward the distal end, the distal end portion of the plate-like portion 3 has higher flexibility.

The material of the first wire rod 71 and the second wire rod 72 is not limited to a specific material, and stainless steel, superelastic alloys, cobalt alloys, noble metals such as gold, platinum, tungsten, or the like, alloys containing these noble metals, and the like can be used as the material.

The first wire rod 71, the second wire rod 72, and the plate-like portion 3 may be made of the same material, or different materials. In the former case, the first wire rod 71, the second wire rod 72, and the plate-like portion 3 have the same rigidity, and thus good reshaping properties, torque transmission performance, and pushing performance are obtained.

In the latter case, the rigidity of the first wire rod 71 and the second wire rod 72 may be higher or lower than that of the plate-like portion 3. When the rigidity of the first wire rod 71 and the second wire rod 72 is higher than that of the plate-like portion 3, the guide wire 1 can have good torque transmission performance and pushing performance. In contrast, when the rigidity of the first wire rod 71 and the second wire rod 72 is lower than that of the plate-like portion 3, the guide wire 1 can have good flexibility.

Solder (brazing material) is preferably used as the fixing portion 9. The fixing portion 9 is not limited to solder, and may be an adhesive. A method of fixing the first wire rod 71 and the second wire rod 72 to the plate-like portion 3 is not limited to the use of the aforementioned fixing materials, and may be welding.

In the exemplary embodiment, the reinforcement portion 7 is provided on one surface of the plate-like portion 3; however, the reinforcement portions 7 may be respectively provided on both surfaces (opposing planar surfaces) of the plate-like portion 3. In this case, it is possible to further increase the torque transmission performance and the pushing performance of the plate-like portion 3.

The shape of each of the first wire rod 71 and the second wire rod 72 is not limited to the shape which is illustrated, and for example, may have a portion that is bent in the longitudinal direction.

Figure 2:
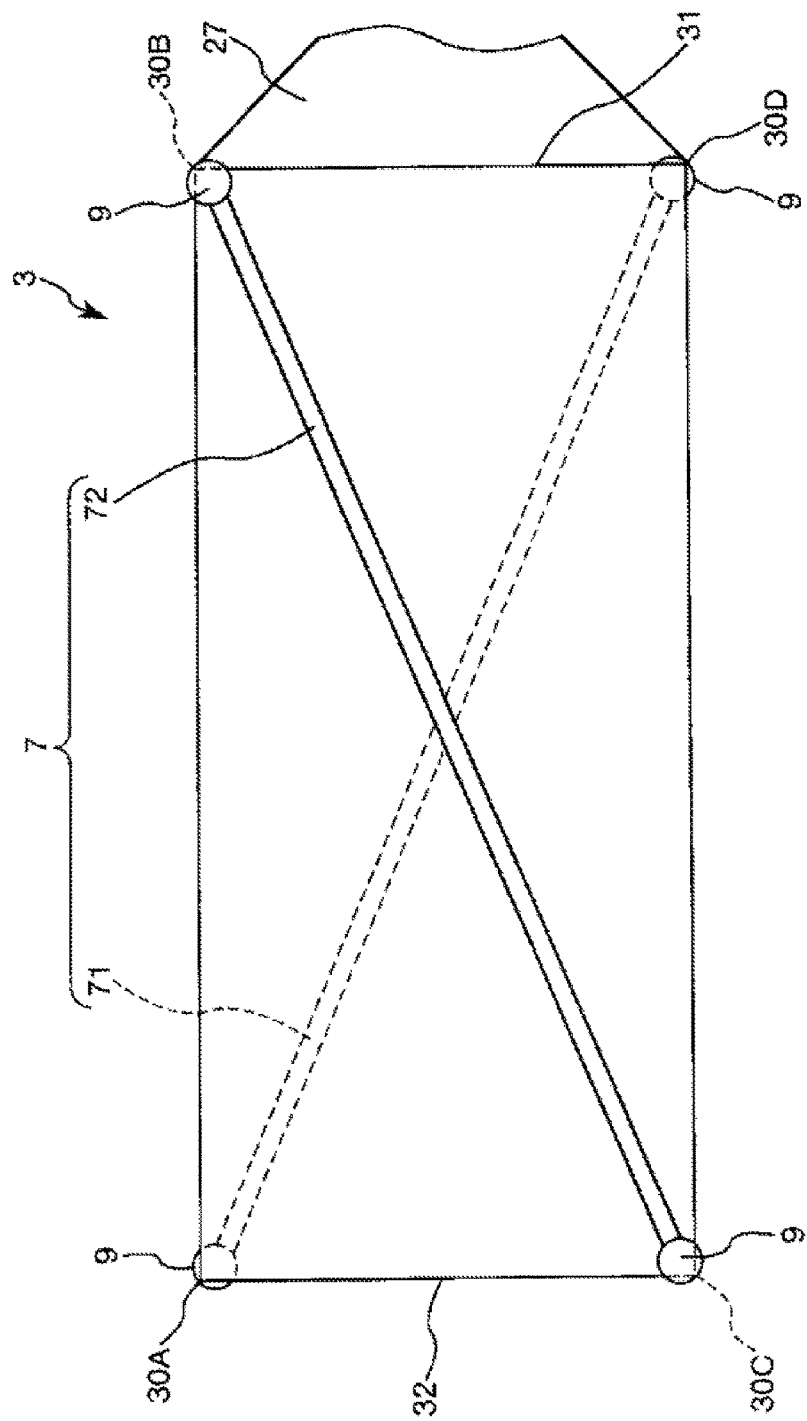
FIG. 2 is a plan view of a plate-like portion of a guide wire according to a second exemplary embodiment of the disclosure.

FIG. 2 is a plan view of a plate-like portion of a guide wire in a second exemplary embodiment of the disclosure.

Hereinafter, the guide wire of the second exemplary embodiment of the disclosure will be described with reference to this drawing. The description will be centered around the points of difference between the first exemplary embodiment and the second exemplary embodiment, and the same items will not be described. For illustrative purposes, in FIG. 2, the right side and the left side in the longitudinal direction of the plate-like portion are respectively referred to as a "proximal end" and a "distal end".

This second exemplary embodiment is the same as the first exemplary embodiment except that the configuration of the reinforcement portion 7 is different from that in the first exemplary embodiment.

As illustrated in FIG. 2, in the second exemplary embodiment, the first wire rod 71 and the second wire rod 72 are respectively provided on different surfaces of the plate-like portion 3. The first wire rod 71 and the second wire rod 72 are inclined in different directions with respect to the axis of the wire main body 10, and intersect each other in a plan view of the plate-like portion 3.

Since the first wire rod 71 and the second wire rod 72 are disposed in this way, flexural rigidity when the plate-like portion 3 is bent toward the front sheet surface of FIG. 2 is balanced with flexural rigidity when the plate-like portion 3 is bent toward the back sheet surface of FIG. 2. Accordingly, the plate-like portion 3 of the second exemplary embodiment has good reshaping properties and operability.

In the illustrated configuration, the first wire rod 71 and the second wire rod 72 intersect each other in the plan view of the plate-like portion 3; however, the first wire rod 71 and the second wire rod 72 may overlap each other in the plan view of the plate-like portion 3. That is, the first wire rod 71 and the second wire rod 72 may be inclined in the same direction with respect to the axis of the wire main body 10.

Figure 3:
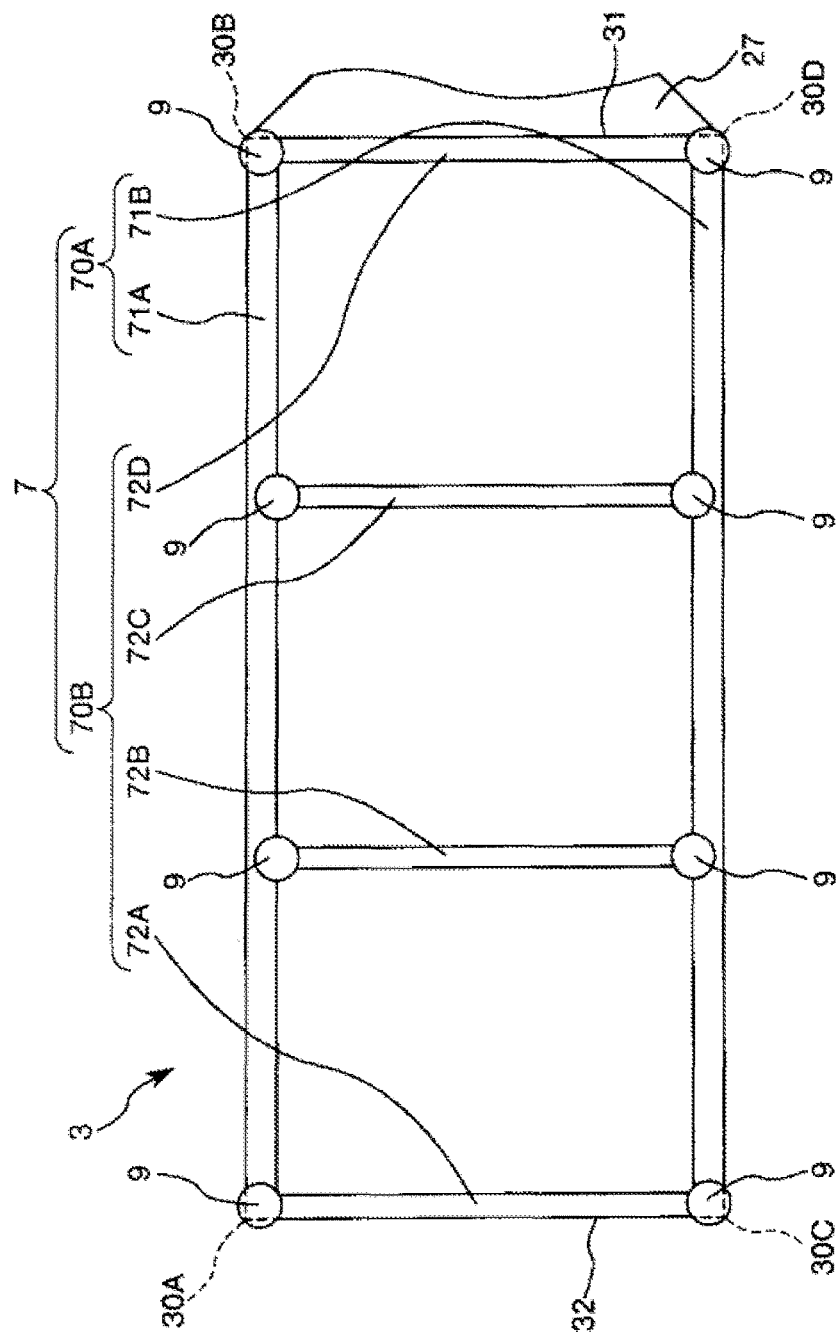
FIG. 3 is a plan view of a plate-like portion of a guide wire according to a third exemplary embodiment of the disclosure.

FIG. 3 is a plan view of a plate-like portion of a guide wire in a third exemplary embodiment of the disclosure.

Hereinafter, the guide wire of the third exemplary embodiment of the disclosure will be described with reference to this drawing. The description will be centered around the points of difference between the first exemplary embodiment and the third exemplary embodiment, and the same items will not be described. For illustrative purposes, in FIG. 3, the right side and the left side in the longitudinal direction of the plate-like portion are respectively referred to as a "proximal end" and a "distal end", and an upper side and a lower side are respectively referred to as the "top", and the "bottom".

This third exemplary embodiment is the same as the second exemplary embodiment except that the configuration of the plate-like portion 3 is different from that in the second exemplary embodiment.

As illustrated in FIG. 3, the reinforcement portion 7 of the third exemplary embodiment has a first reinforcement portion 70A that extends in the longitudinal direction of the plate-like portion 3, and a second reinforcement portion 70B that extends in a lateral direction of the plate-like portion 3. The first reinforcement portion 70A is mainly responsible for increasing the pushing performance of the guide wire 1.

The first reinforcement portion 70A is configured to include wire rods 71A and 71B which are respectively provided along edge portions that face each other in the lateral direction of the plate-like portion 3. A distal end portion of the wire rod 71A is fixed to the corner 30A, and a proximal end portion thereof is fixed to the corner 30B. In contrast, a distal end portion of the wire rod 71B is fixed to the corner 30C, and a proximal end portion thereof is fixed to the corner 30D.

The second reinforcement portion 70B has four wire rods 72A, 72B, 72C, and 72D which are provided while being equally spaced in the longitudinal direction of the plate-like portion 3. The wire rods 72A, 72B, 72C, and 72D are sequentially provided from the distal end side. The second reinforcement portion 70B is mainly responsible for increasing the torque transmission performance of the wire guide 1.

The wire rod 72A is provided along an edge portion that is positioned at the distal end of the plate-like portion 3. An upper end portion of the wire rod 72A along with the distal end portion of the wire rod 71A is fixed to the corner 30A. A lower end portion of the wire rod 72A along with the distal end portion of the wire rod 71B is fixed to the corner 30C.

The wire rod 72B is provided in the middle of the plate-like portion 3 in the longitudinal direction of the plate-like portion 3. An upper end portion of the wire rod 72B along with a middle portion of the wire rod 71A in a longitudinal direction of the wire rod 71A is fixed to an upper-end edge portion of the plate-like portion 3. A lower end portion of the wire rod 72B along with a middle portion of the wire rod 71B in a longitudinal direction of the wire rod 71B is fixed to a lower-end edge portion of the plate-like portion 3.

The wire rod 72C is provided in the middle of the plate-like portion 3 in the longitudinal direction of the plate-like portion 3. An upper end portion of the wire rod 72C along with a middle portion of the wire rod 71A in the longitudinal direction of the wire rod 71A is fixed to the upper-end edge portion of the plate-like portion 3. A lower end portion of the wire rod 72C along with a middle portion of the wire rod 71B in the longitudinal direction of the wire rod 71B is fixed to the lower-end edge portion of the plate-like portion 3.

The wire rod 72D is provided along an edge portion that is positioned at the proximal end of the plate-like portion 3. An upper end portion of the wire rod 72D along with the proximal end portion of the wire rod 71A is fixed to the corner 30B. A lower end portion of the wire rod 72D along with the proximal end portion of the wire rod 71B is fixed to the corner 30D.

The wire rods 71A, 71B, 72A, 72B, 72C, and 72D are disposed in the shape of a ladder in the plan view of the plate-like portion 3.

When a rotating force is applied to the proximal end portion of the guide wire 1, the rotating force is transmitted from the proximal end side, to the second wire 4, to the first wire 2, and then to the distal end side of the guide wire 1. When the rotating force is transmitted to the proximal end 31 of the plate-like portion 3, the rotating force is sufficiently and reliably transmitted to the distal end of the plate-like portion 3 via the wire rods 71A, 71B, 72A, 72B, 72C, and 72D.

When a pushing force is applied from the proximal end portion of the guide wire 1 to the distal end portion of the guide wire 1, the pushing force is transmitted from the proximal end side, to the second wire 4, to the first wire 2, and then to the distal end side of the guide wire 1. When the pushing force is transmitted to the proximal end 31 of the plate-like portion 3, the pushing force is transmitted from the proximal end 31 of the plate-like portion 3 to the distal end 32. The pushing force transmitted to the proximal end 31 of the plate-like portion 3 is sufficiently transmitted to the distal end of the plate-like portion 3 via the wire rods 71A, 71B, 72A, 72B, 72C, and 72D. Accordingly, the plate-like portion 3 has good pushing performance (pushability).

The guide wire of the disclosure herein has been described based on the illustrated exemplary embodiments; however, the disclosure is not limited to those embodiments, and configurational elements can be replaced with arbitrary elements having the same functions. Other arbitrary configurational elements may be added according to the disclosure.

In the exemplary embodiments, the reinforcement portion is made of a wire rod; however, the disclosure is not limited to that configuration, and for example, the reinforcement portion may be configured as a net-shaped member or the like.

In the exemplary embodiments, the reinforcement portion and the plate-like portion are formed independently from each other; however, the reinforcement portion and the plate-like portion may be integrally formed. In this case, it is possible to omit a step of fixing the reinforcement portion to the plate-like portion.

The guide wire of the disclosure herein includes the wire main body that has the plate-like portion in the distal end portion of the wire main body, and the reinforcement portion that is provided on at least one surface of the plate-like portion, and reinforces the plate-like portion.

According to the disclosure, it is possible to easily and reliably shape the distal end portion of the guide wire in a desired shape while sufficiently ensuring the flexibility of the distal end portion of the guide wire, and to provide the guide wire with good torque transmission performance and pushing performance.

In particular, it is possible to ensure the flexibility, the torque transmission performance, and the pushing performance of the distal end portion of the guide wire by providing the linear reinforcement portion on at least one surface of the plate-like portion.

Accordingly, the guide wire of the disclosure has industrial applicability.

The detailed description above describes a guide wire. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A guide wire comprising:
a wire main body including a plate-like portion in a distal end portion of the wire main body, the plate-like portion having a distal-most end and a proximal-most end; and
a reinforcement portion provided on at least one surface of the plate-like portion, and which reinforces the plate-like portion;
wherein the reinforcement portion extends from the distal-most end to the proximal-most end of the plate-like portion;
wherein the reinforcement portion includes two wire rods;
wherein the plate-like portion defines a first planar surface and a second planar surface; and
wherein each of the two wire rods is provided on the first planar surface of the plate-like portion, and the two wire rods intersect each other at a center portion of the plate-like portion.

2. The guide wire according to claim 1,
wherein the reinforcement portion includes opposing end portions and the reinforcement portion is fixed to the plate-like portion at only the opposing end portions.

3. The guide wire according to claim 1,
wherein the plate-like portion is formed in a ribbon shape, and
wherein the reinforcement portion is provided on a diagonal line of the plate-like portion.

4. The guide wire according to claim 1,
wherein rigidity of the reinforcement portion is the same as that of the plate-like portion.

5. The guide wire according to claim 1,
wherein rigidity of the reinforcement portion is different from that of the plate-like portion.

6. The guide wire according to claim 1,
wherein the reinforcement portion is configured as a member that is separate from the plate-like portion.

7. The guide wire according to claim 1,
wherein the reinforcement portion is formed integrally with the plate-like portion.

8. The guide wire according to claim 1, further comprising:
a coil that covers the plate-like portion and the reinforcement portion.

9. A guide wire comprising:
a wire main body including a first wire disposed on a distal end side of the wire main body and a second wire disposed on a proximal end side of the wire main body, the first wire being joined to the second wire, and the first wire including a planar portion having a first planar surface and a second planar surface; and
a reinforcement portion provided on at least one of the first planar surface and the second planar surface of the planar portion;
wherein the reinforcement portion includes a first wire rod and a second wire rod;
wherein the first wire rod and second wire rod each include a first terminal end portion, a second terminal end portion and a rod body portion extending therebetween,
wherein the first wire rod and second wire rod are secured to the at least one of the first planar surface and the second planar surface of the planar portion only at the first terminal end portion and the second terminal end portion such that the rod body portion is not secured to the at least one of the first planar surface and the second planar surface of the planar portion, the rod body portion thus being configured to approach and move away from the at least one of the first planar surface and the second planar surface of the planar portion;
wherein the first wire rod extends diagonally across the first planar surface of the planar portion from an upper left corner to a lower right corner of the planar portion and the second wire rod extends diagonally across the first planar surface of the planar portion from a lower left corner to an upper right corner of the planar portion; and
wherein the first wire rod and the second wire rod cross and overlap one another at a center portion of the first planar surface of the planar portion.

10. The guide wire according to claim 9, wherein the reinforcement portion including the first wire rod and the second wire rod defines a first reinforcement portion provided on the first planar surface of the planar portion.

* * * * *